US00PP09890P

United States Patent [19]

Ledbetter et al.

[11] Patent Number: Plant 9,890

[45] Date of Patent: May 13, 1997

[54] APRICOT CV. ROBADA

[75] Inventors: Craig A. Ledbetter, Clovis; David W. Ramming, Fresno, both of Calif.

[73] Assignee: The United States of America as represented by the Secretary of Agriculture, Washington, D.C.

[21] Appl. No.: 502,516

[22] Filed: Jul. 14, 1995

[51] Int. Cl.[6] ..... A01H 5/00

[52] U.S. Cl. ..... Plt./39

[58] Field of Search ..... Plt./39

*Primary Examiner*—James R. Feyrer

*Attorney, Agent, or Firm*—M. Howard Silverstein; John D. Fado; Margaret A. Connor

[57] ABSTRACT

A new and distinct variety of apricot tree which is characterized by having the following combination of outstanding features that are desirable in a new variety; fruit with an unusually large amount of red skin color in the form of a bright red blush, fruit with good flavor and high eating quality, self-compatible flowers which require no cross-pollination, and fruit with firm flesh, giving good handling and shipping qualities.

1 Drawing Sheet

BACKGROUND OF THE NEW VARIETY

The present invention relates to a new and distinct variety of apricot tree, which will hereinafter be denominated varietally as 'Robada.' More particularly, the invention relates to the discovery and asexual propagation of apricot *Prunus armeniaca* L. cv. 'Robada.' The new variety is a fresh market apricot for use in local markets as well as for long distance shipping.

The new variety of apricot tree was produced from a cross between the apricot variety 'Orangered' (seed parent) and apricot selection K113-40 (pollen parent) grown in a research orchard located near Parlier, Calif. The pollen parent originated in the U.S. Department of Agriculture (USDA) Agricultural Research Service (ARS) apricot breeding program. Planned hybridizations, four generations removed from the original apricot varieties 'Blenheim', 'Blush' and 'Perfection', resulted in the selection of K113-40.

The first generation seedlings from the 'Orangered'× K113-40 hybridization were grown and maintained in a research orchard located near Parlier, Calif. When these trees became reproductively fit, close attention was paid to desirable fruit characteristics. The present variety was then selected from among all other seedlings in this progeny, due to its unique combination of desirable fruit characteristics. This tree was then asexually propagated to other rootstocks, where it remained true-to-character in other orchard environments.

The new variety of apricot tree has been asexually reproduced by both dormant grafting and June-budding in the USDA-ARS research orchard in Fresno, Calif., and are identified by Selection Identification Number K106-2. Trees reproduced by both of these means have shown that the characteristics run true to the original seedling tree. Desirable fruit characteristics are therefore transmitted through succeeding propagations.

BRIEF DESCRIPTION OF THE DRAWING

The accompanying drawing is a color photograph showing typical stems, leaves, fruit, dormant budsticks, and stones of the new variety. The photograph was taken shortly after fruit harvest, and the colors are as representative as possible for the fruit and vegetative characteristics of the new variety. Mature fruit have been sectioned and positioned to demonstrate the typical form and coloration associated with the various profiles. Both upper and lower leaf surfaces are shown for mature leaves of current season's growth. A slight curling of the mature leaves is typical for this new apricot grown in the environment of the central San Joaquin Valley, Calif. Shoot terminals have been shown to demonstrate their strong red coloration which is typical of this new apricot.

SUMMARY OF THE INVENTION

The new variety cv. 'Robada' may be distinguished from other presently available commercial apricot cultivars by a combination of characteristics, including fruit with an unusually large amount of red skin color in the form of a bright red blush, fruit with good flavor and high eating quality, self-compatible flowers which require no cross-pollination, and fruit with firm flesh, giving good handling and shipping quality.

The new variety of apricot is most similar to the commercial apricot variety 'Castlebrite' (unpatented) by having similar dates of flowering and by being harvested approximately seven days after 'Castlebrite.' It is distinguished therefrom and an improvement thereon in a number of fruit characteristics. Both flesh and skin color of the new variety are more deeply orange colored when compared to the skin and flesh of 'Castlebrite' in fruit samples of similar fruit maturity. Skin overcolor is a deeper red, and the percentage of overcolor is greater for the new apricot variety compared to 'Castlebrite.' Fruit soluble solids are higher, and fruit acidity is lower in the new variety than in 'Castlebrite' when comparing fruit samples of similar maturity.

The new variety also differs substantially from its seed parent 'Orangered.' It is significantly larger and ripens approximately 25 days prior to 'Orangered' in the central San Joaquin Valley, Calif. Furthermore, the bloom period of the new variety is distinguished from that of 'Orangered' by occurring approximately 20 days prior to that of 'Orangered.'

DETAILED DESCRIPTION OF THE NEW VARIETY

The following is a detailed description of the new and distinct variety of apricot tree grown in the environment of Fresno, Calif. and is believed to apply to plants of the variety grown under similar conditions of soil and climate elsewhere. Where numeric values presented in the Detailed Description are followed by a "±" they represent the arithmetic mean plus or minus one standard deviation. Color code designations are by reference to *The Royal Horticultural Society Colour Chart,* The Royal Horticultural Society, London, Flower Council of Holland, Leiden, (1986). Common color names are also used occasionally.

TREE

Size: Large.
Vigor: Vigorous.
Growth: Open and spreading growth habit.
Foliage density: Moderate amount of brush.
Production: Average fruit production.
Bearer: Fruit productivity varies between years.
Trunk: (Evaluation taken 20 cm above the soil surface).
*Size.*—Medium.
*Texture.*—Average roughness.
*Color.*—Fan 4, No. 199, D (grey-brown).
Branches: (Evaluation from 5 cm diameter branches).
*Texture.*—Smooth.
*Lenticles.*—Typically fewer than average in number and generally average about 4 mm in length. Lenticles are present on branches ranging from mature current season's growth to wood of approximately 6 cm in diameter.
Shoot color of current season's growth from shoots ranging from 0.5–1.5 cm diameter: Fan 4, No. 187, B (grey-purple). Shoot terminals are strongly red tingd. Fan 1, No. 46, A (red).
Leaves: (Measurements were taken from fully mature leaves of current season growth.)
*Size.*—Leaf blade length ranges from about 6.0 to 8.4 cm, with an average length of about 7.2 (7.2±0.6 cm). Leaf blade width ranges from about 5.4 to 8.6 cm, with an average width of about 7.0 (7.0±0.8 cm). Leaf blade thickness ranges from about 0.23 to 0.47 mm, with an average thickness of about 0.35 (0.35±0.06 mm).
*Form.*—Broadly cordate.
*Apex.*—Acuminate.
*Base.*—Generally obtuse.
*Texture.*—Smooth.
*Margin.*—Serrate. Average of 6.2±0.9 serrations/cm as measured at mid-blade. Frequency of serrations decreases substantially towards the leaf base. In 'Orangered,' serrations/cm averaged 4.6±0.8.
*Color.*—Upper surface: Fan 3, No. 146, A (yellow-green). Lower surface: Fan 3, No. 148, B (yellow green).
*Petiole.*—Red coloration (Fan 2, No. 59, A) generally extends into the leaf midrib as well as into the major secondary veins of the leaves. Average petiole length: 3.9±0.3 cm. 'Orangered' averaged 3.2±0.8 cm. Average petiole width: 1.53±0.1 mm.
*Stipules.*—Present and fancy in new growth, abscising as leaves mature. Average length: 8.8±1.7 mm.
*Glands.*—Generally globose in form. Location and number varies substantially among leaves. Average of 3.0±1.2 glands/leaf.

FLOWERS

Flower buds:
*Size.*—Average in size in this class.
*Length.*—Average.
*Form.*—Plump.
*Hardiness.*—Abundant flowering in trees throughout the San Joaquin Valley, Calif.
Flowers:
*Blooming period.*—Generally a medium date of bloom in relation to the range of bloom dates for other commercial apricot varieties. Feb. 8, 1995–Feb. 22, 1995 in orchards of the central San Joaquin Valley, Calif. The blooming period for 'Orangered' was from Mar. 7, 1995–Mar. 20, 1995.
*Size.*—Small to average.
*Petal color.*—Evaluated one day pre-anthesis at center of petal whorl. Fan 2, No. 62, C (red-purple).
*Pollen.*—Present and self-compatible.
*Pollen color.*—Evaluated after screening and drying, within a glass vial. Fan 1, No. 5, B (yellow).

FRUIT

Maturity when described: Measurements were taken from fruit having an average flesh firmness of 19.17 N (4.3±1.1 lb) when measured with a hand-held penetrometer equipped with an 8 mm tip on a freshly cut flesh surface (skin removed).
Date of first picking: May 18, 1995.
Date of last picking: May 26, 1995.
Size: Fruit mass ranges from about 90 to 125 g, with an average mass of about 112.4 g (112.4±13.1 g). Fruit mass at harvest can be manipulated by the degree of fruit thinning. In 'Orangered' the average mass was 48±3.2 g (harvest date: Jun. 20, 1995).
*Diameter.*—Fruit diameters correlate with fruit mass and vary proportionally depending upon the crop load. The following diameter measurements are for fruit with an average mass of 112.4 g. Average diameter axially: 62.3±2.4 mm. Average diameter transversely in suture plane: 67.0±2.1 mm.
Form: Oblong.
Suture: Visible from apex to base with a pronounced depression at apical end.
Ventral surface: Rounded with generally symmetrical lips.
Cavity:
*Axial length perpendicular to suture.*—19.2±1.3 mm.
*Axial length in suture plane.*—30.6±1.6 mm.
*Transverse length.*—34.2±1.52 mm.
Base: Generally rounded to ellipsoid with elliptic compression in the same plane as suture.
Apex: A depression is usually present at the apex which encompasses the pistil point.
Pistil point: Depressed.
Stem: The pedicle is of average thickness and length. It generally pulls free from the stone.
Skin:
*Astringency.*—Slight amount noted particularly in areas of extreme overcolor.
*Thickness.*—Average.
*Texture.*—Average.
*Tenacity.*—Tenacious to the flesh.
*Tendency to crack.*—Low.
*Pubescence.*—Scant and short, no tendency to roll-up when rubbed.
*Color.*—Fan 4, No. 167, C (greyed-orange).
*Overcolor.*—Fan 1, No. 42, B (red). The intensity of red overcolor and the amount of overcolor on the fruit surface area are dependent upon the ecological and cultural conditions in which this variety is grown . Overcolor may be further manipulated by cultural practices such as leaf removal. Under the ecological conditions present in the central San Joaquin Valley of California, overcolor may be present on 0% of the fruit surface area (no direct exposure to sun) to approximately 40% of the fruit surface area (full sun exposure).

Flesh:

*Color.*—Fan 4, No. 165, B (greyed-orange).
*Juice.*—Moderate juiciness.
*Texture.*—Finely grained.
*Fibers.*—Few and tender.
*Ripens.*—Evenly.
*Flavor.*—A tasteful balance between sugars, acids and aromatics.
*Eating quality.*—Exceptionally high.
*Brix.*—16.8±1.3° Brix.
*Acidity.*—0.72±0.02%.

STONE

Measurements were made from stones taken from fruit having an average fruit mass of 112.4 g.)

Attachment: Freestone, slight attachment of flesh fibers along suture.

Size:

*Average mass.*—4.35±0.30 g.
*Average length.*—33.47±1.19 mm.
*Average width.*—26.29±1.58 mm.
*Average thickness perpendicular to suture plane.*—16.29±0.43 mm.

Apex: Gently rounded curve to an apical tip. Tip is prominent but not sharp.

Base: Flattened to slightly concave.

Surface: Generally pebbled surface with only a few pits. Lighter colored irregular markings resembling venation are interpersed randomly across stone surface.

Ridges: Prominent ridges (wings) are present along both sides of suture plane.

Tendency to split: None.

Color: Fan 4, No. 165, C (greyed-orange).

Kernel:

*Form.*—Generally not well-filled with somewhat irregular shape. Rudimentary pellicle from aborted embryo is also usually apparent.
*Taste.*—Sweet.
*Viable.*—Viable.
*Average width.*—14.07±0.84 mm.
*Average length.*—17.84±1.92 mm.

Pellicle color (when fresh, air dried): Fan 1, No. 25, D (orange).

Amygdalin: Not detectable by taste.

Use: Fresh market apricot for use in local markets as well as for long distance shipping.

Keeping quality: Good.

The present new variety of apricot tree, its flowers, foliage, and fruit herein described may vary in slight detail due to climatic, soil conditions, and cultural practices under which the variety may be grown; the present description is that of the variety grown under the ecological conditions prevailing near Fresno Calif.

What is claimed is:

1. A new and distinct variety of apricot tree, substantially as illustrated and described, characterized by fruit with an unusually large amount of red skin color in the form of a bright red blush, fruit with good flavor and high eating quality, self-compatible flowers which require no cross-pollination, and fruit with firm flesh giving good handling and shipping qualities.

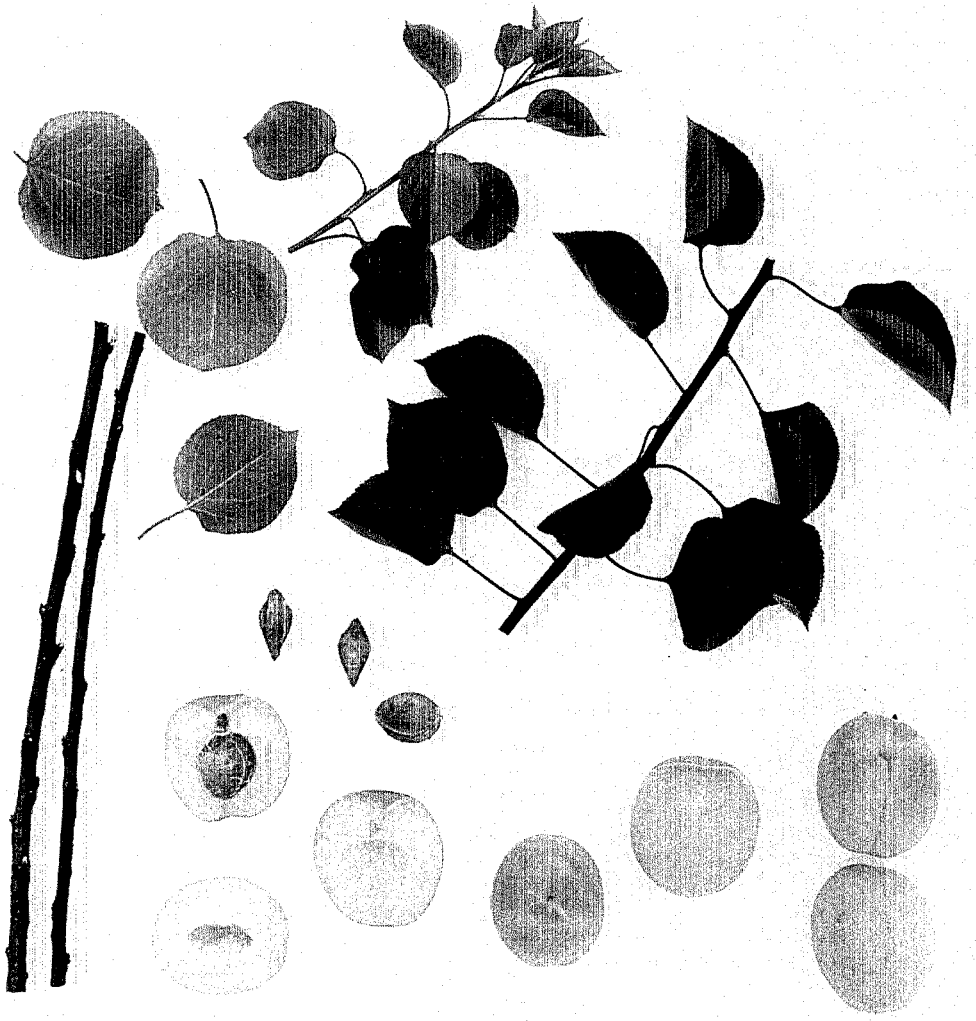

* * * * *